United States Patent [19]

Hemmi et al.

[11] Patent Number: 5,430,025

[45] Date of Patent: * Jul. 4, 1995

[54] ELASTASE-INHIBITING PEPTIDES BEARING A C-TERMINAL TRIFLUOROMETHYLKETONE MOIETY

[75] Inventors: Keiji Hemmi, Tsukuba; Ichiro Shima, Moriyamachi; Keisuke Imai, Tsukuba; Hirokazu Tanaka, Tsuchiura, all of Japan

[73] Assignee: Fujisawa Pharmaceutical Co., Ltd., Osaka, Japan

[*] Notice: The portion of the term of this patent subsequent to Mar. 22, 2011 has been disclaimed.

[21] Appl. No.: 158,981

[22] Filed: Nov. 30, 1993

Related U.S. Application Data

[62] Division of Ser. No. 805,610, Dec. 12, 1991, Pat. No. 5,296,591.

[30] Foreign Application Priority Data

Dec. 31, 1990 [GB] United Kingdom ............... 9028231
Sep. 16, 1991 [GB] United Kingdom ............... 9119713

[51] Int. Cl.$^6$ .............................................. A61K 38/06
[52] U.S. Cl. .................................... 514/18; 530/331; 564/153; 544/164; 544/168
[58] Field of Search .............. 530/331, 332; 564/153, 564/51; 548/537; 544/164, 168; 562/435, 439, 450; 560/20, 34, 41; 514/18

[56] References Cited

U.S. PATENT DOCUMENTS

| | | | |
|---|---|---|---|
| 4,910,190 | 3/1990 | Bergeson | 514/19 |
| 5,296,591 | 3/1994 | Hemmi | 530/331 |

FOREIGN PATENT DOCUMENTS 0189305 7/1986 European Pat. Off.
0276101 7/1988 European Pat. Off.
0369391 5/1990 European Pat. Off.

OTHER PUBLICATIONS

Skiles et al., *Chemical Abstracts*, 116(11), 1992, Abst. No. 106736y.

Primary Examiner—Jill Warden
Assistant Examiner—David Lukton
Attorney, Agent, or Firm—Oblon, Spivak, McClelland, Maier & Neustadt

[57] ABSTRACT

Trifluoromethylketone compounds of the formula:

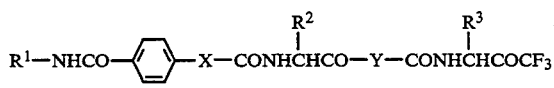

wherein
$R^1$ is $C_{1-6}$ alkyl which has one or two substituents selected from carboxy, esterified carboxy and di-$C_{1-6}$ alkylcarbamoyl; phenyl($C_{1-6}$)alkyl, the phenyl moiety of which may have halogen or nitro or amino substituents and the alkyl moiety of which may have carboxy or esterified carboxy substituents; halo-phenyl; morpholino; or morpholino($C_{1-6}$)alkyl, $R^2$ and $R^3$ are each $C_{1-6}$ alkyl, X is —or —NH—, and

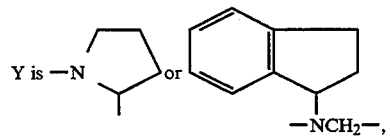

and pharmaceutically acceptable salts thereof are useful for inhibiting human elastase.

6 Claims, No Drawings

ELASTASE-INHIBITING PEPTIDES BEARING A C-TERMINAL TRIFLUOROMETHYLKETONE MOIETY

This is a division of application Ser. No. 07/805,610, filed on Dec. 12, 1991, now U.S. Pat. No. 5,296,591.

This invention relates to new trifluoromethylketone derivatives.

More particularly, this invention relates to new trifluoromethylketone derivatives and their pharmaceutically acceptable salts which have an human leukocyte elastase-inhibiting activity, to processes for preparation thereof, and to a pharmaceutical composition comprising the same and to a method of use thereof.

The new trifluoromethylketone derivatives of this invention are represented by the following formula (I):

wherein
$R^1$ is lower alkyl which has one or two substituents selected from carboxy, esterified carboxy and di-lower alkylcarbamoyl, phenyl(lower)alkyl, the phenyl moiety of which may have halogen or nitro or amino and the alkyl moiety of which may have carboxy or esterified carboxy, halo-phenyl, morpholino or morpholino(lower)alkyl, $R^2$ and $R^3$ are each lower alkyl, X is —or —NH— and

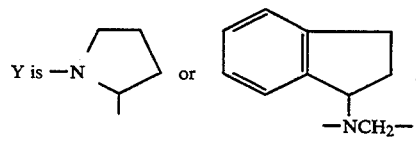

According to this invention, the new trifluoromethylketone derivatives (I) and salts thereof can be prepared by various processes which are illustrated by the following reaction schemes:

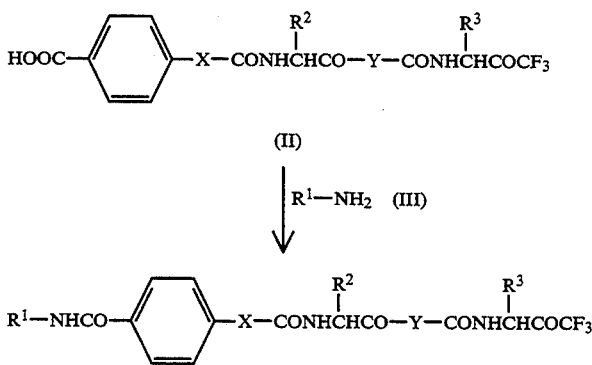

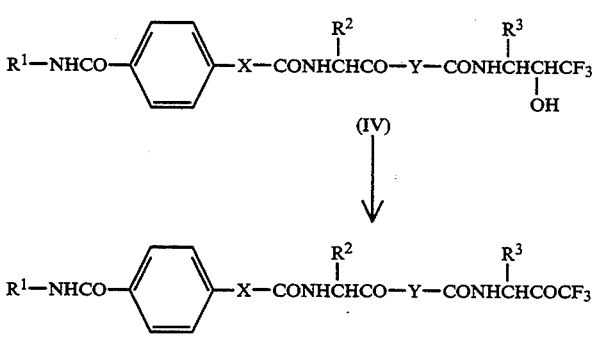

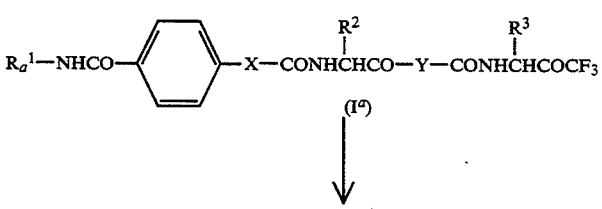

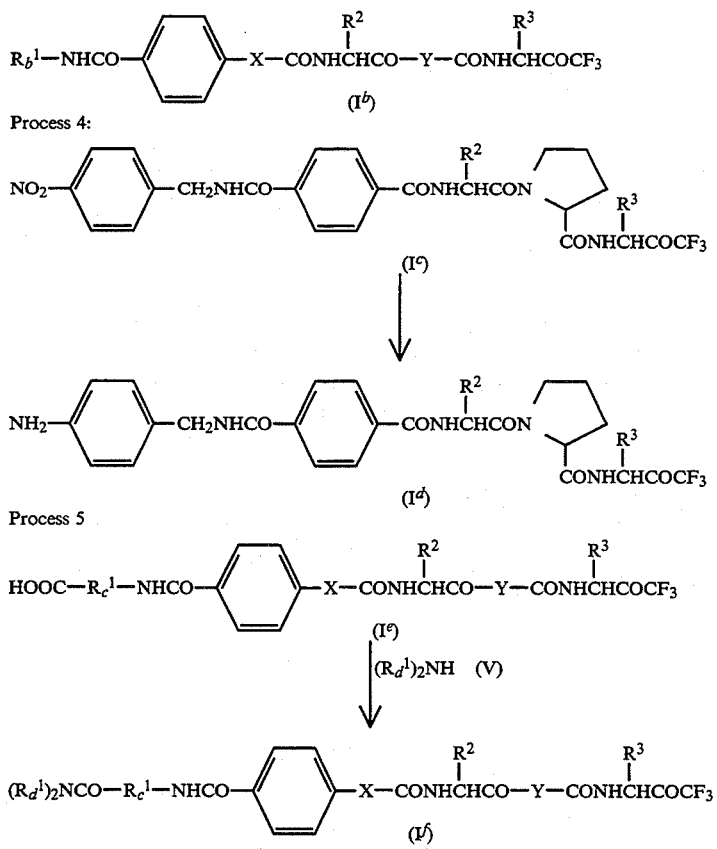

In the above formulae, $R_a^1$ is mono- or di- esterified carboxy(lower)alkyl and $R_b^1$ or mono- or di- carboxy(lower)alkyl, $R_c^1$ is lower alkylene $R_d^1$ is lower alkyl, and $R^1$ to $R^3$, X and Y are each as defined above.

A pharmaceutically acceptable salt of the new trifluoromethylketone derivatives of the formula (I) may include a salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt or the like, and an acid addition salt with organic or inorganic acid such as methane sulfonate, hydrochloride, sulfate, nitrate, phosphate or the like.

Preferred examples and illustrations of the various definitions, in the above descriptions, which the present invention includes within the scope thereof are explained in detail as follows.

The term "lower" is intended to mean 1 to 6 carbon atoms, unless otherwise indicated.

Preferred examples of "halogen" is fluorine, chlorine, bromine and iodine.

Preferred examples of "lower alkyl" may include a residue of straight and branched alkane having 1 to 6 carbon atoms such as methyl, ethyl, propyl, isopropyl, butyl, isobutyl, t-butyl, pentyl, neopentyl, hexyl and the like, and preferably the one having 1 to 4 carbon atom(s).

Preferred examples of "esterified carboxy" may include an alkyl ester, i.e. alkoxycarbonyl such as lower alkoxycarbonyl (e.g. methoxycarbonyl, ethoxycarbonyl, propoxycarbonyl, butoxycarbonyl, tert-butoxycarbonyl, etc.) and a phenyl(lower)alkyl ester, i.e. phenyl(lower)alkoxycarbonyl such as benzyloxycarbonyl and a benzoyl(lower)alkyl ester, i.e. benzoyl(lower)alkoxycarbonyl such as benzoylmethoxycarbonyl, and the like.

Preferred examples of "lower alkylene" may include methylene, ethylene, propylene, isopropylene and the like.

Preferred examples of "di-lower alkylcarbamoyl" may include N,N-dimethylcarbamoyl, N,N-diethylcarbamoyl and the like.

Processes for preparing the object compound (I) or its salts of this invention are explained in detail in the following.

In the explanation of Processes 1 to 5 as follows, salts of Compounds (I), ($I^a$) to ($I^f$), and (II) to (V) may include the same as those exemplified as pharmaceutically acceptable salt of triftuoromethylketone derivatives (I) as illustrated hereinbefore.

(1) Process 1: Compound (II)+Compound (III)→ Compound (I)

Compound (I) and its salt can be prepared by reacting Compound/II) or its salt with a Compound (III) or its salt.

The reaction of this process can be conducted as follows.

That is, in one case, as the first step, the carboxy group of Compound (II) or its salt is usually activated in a conventional manner, for example, in the form of its acid halide, azide, acid anhydride or a mixed anhydride, activated ester, and the like, and is reacted with the Compound (III) to give Compound (I), and in the other case, the Compound (II) or its salt is reacted with the Compound (III) or its salt directly in the presence of a conventional condensing agent such as N,N-dicyclohexylcarbodiimide, 1-ethyl-3-(3-dimethylaminopropyl)carbodiimide and the like.

This reaction is preferably carried out in a solvent such as N,N-dimethylformamide, methylene chloride, chloroform, tetrahydrofuran, dioxane, ethyl acetate, methanol, ethanol, water or the like under ice-cooling to at ambient temperature and the reaction in the presence of a condensing agent is usually carried out in an anhydrous, but not critical, conditions.

(2) Process 2: Compound (IV)→Compound (I)

The Compound (I) and its salt can be prepared by oxidizing the Compound (IV) or its salt.

The oxidation is carried out by a conventional method using an oxidizing agent which can be applied to converting a hydroxymethyl group to a carbonyl group such as potassium permanganate, chromic compound (e.g. chromic acid, sodium chromate, dichromic acid, sodium dichromate, pyridinium chlorochromate, pyridinium dichromate, etc.), Swern reagent (dimethylsulfoxide and oxalylchloride), Jones reagent and the like.

The reaction is usually carried out in a conventional solvent such as water, acetone, dioxane, dimethylformamide, pyridine or any other organic solvents which do not adversely influence to the reaction, or a mixture thereof.

This reaction is preferably carried out under somewhat milder condition such as under cooling, at room temperature or under warming.

(3) Process 3: Compound ($I^a$)→Compound ($I^b$)

The Compound ($I^b$) and its salt can be prepared by subjecting the Compound ($I^a$) or its salt to de-esterification reaction.

The de-esterification reaction is carried out by a conventional method such as hydrolysis, reduction or the like, details of which are explained in the following:

1) Hydrolysis:

Hydrolysis is preferably carried out in the presence of an acid or base.

Suitable acid includes an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, sodium bicarbonate, calcium hydroxide, etc.), ammonium hydroxide or the like; an organic base such as an alkoxide or phenoxide of the above metal (e.g. sodium ethoxide, sodium methoxide, etc., an amine such as mono-, di or tri- alkylamine (e.g. methylamine, ethylamine, N,N-dimethyl-1,3-propanediamine, trimethylamine, triethylamine, etc.) or the like.

The hydrolysis is preferably conducted under somewhat milder conditions such as under cooling or under warming in a solvent which does not have adverse influence to the reaction, e.g. water, a hydrophilic solvent such as alcohol (e.g. methanol, ethanol, propanol, etc.), acetone, N,N-dimethylformamide, etc. A liquid abovementioned acid and base can also be used as a solvent.

2) Reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, etc.).

Suitable catalysts to be used in catalytic reduction are conventional ones such as platinum catalysts (e.g. platinum plate, spongy platinum platinum black, colloidal platinum, platinum oxide, etc.], palladium catalysts (e.g. spongy palladium, palladium black, palladium oxide, palladium on carbon, colloidal palladium, etc.), or the like.

The reduction is usually carried out in a solvent such as water, an alcohol (e.g. methanol, ethanol, etc.) or the like.

The reduction is preferably carried out under somewhat milder conditions such as under cooling, at room temperature or under warming.

(4) Process 4: Compound ($I^c$)→Compound ($I^d$)

The Compound ($I^d$) or its salt can be prepared by reducing the Compound ($I^c$) or its salt.

The reduction including chemical reduction and catalytic reduction is carried out in a conventional manner.

Suitable reducing agents may include the same as those exemplified in Process 3.

The reduction is usually carried out in a solvent such as water, an alcohol (e.g. methanol, ethanol, etc.) or the like.

The reduction is preferably carried out under somewhat milder conditions such as under cooling, at room temperature or under warming.

(5) Process 5: Compound ($I^e$)+Compound (V)→Compound ($I^f$)

Compound (I) and its salt can be prepared by reacting Compound ($I^e$) or its salt with Compound (V) or its salt.

The reaction is carried out by substantially the same method of that of Process 1.

Pharmaceutically acceptable salts of the trifluoromethylketone derivatives (I) can be prepared by a conventional method, i.e., by treating the Compound (I) with an acid or a base. Suitable examples of the acid or base may include the same as those exemplified in the explanation of "Hydrolysis" of Process 3.

Starting Compounds (II) to (V) each include new compounds and can be prepared by Preparations as described hereinafter and by the similar methods thereto.

The object Compound (I) including Compounds ($I^a$) to ($I^f$) and starting Compounds (II) and (IV) include one or more isomers due to the asymmetric carbon atoms and all of such isomers are included within the scope of this invention.

According to this invention, there can be obtained a mixture of diastereoisomers due to the presence of compounds bearing both R and S configurations at the chiral center marked with A of the formula as mentioned below, and there can also be obtained an optically pure compound.

It is to be noted that said optically pure compound changes to a mixture of said diastereoisomers in an aqueous and/or organic solution.

$$R^1-NHCO-\underset{}{\bigcirc}-X-CONHCHCO-Y-CONH\underset{A}{CH}COCF_3$$
$$\phantom{R^1-NHCO-\bigcirc-X-CON}\overset{R^2}{|}\phantom{CO-Y-CONH}\overset{R^3}{|}$$

Further, it is to be noted that the object compound (I) of this invention provides a hydrate form in an aqueous solution, which is included within the scope of this invention.

The trifluoromethylketone derivatives (I) and pharmaceutical acceptable salt thereof have a human leukocyte elastase-inhibiting activity and is useful as human leukocyte elastase inhibitors for treating or preventing degenerative diseases for example, pulmonary emphysema, atherosclerosis, rheumatoid arthritis, arthrosclerosis, osteoarthritis, psoriasis, pancreatitis, periodontosis, pulmonary fibrosis, cystic fibrosis, chronic bronchitis, bronchiectasia, diffuse panbronchiolitis, respiratory injury, adult respiratory distress syndrome and the like, and further is useful for treatment or prevention of asthma, graft rejection nephritis, hydroa, disseminated intravascular coagulation, shock, systemic lupus erythematosus, clone disease, ischemia-reperfusion injury, chronic obstructive pulmonary disease (COPD), premature rupture of the membrane (PROM), corneal sarring or fibroblast proliferation (ocular coagulation, burns, mechanical and chemical injury, kerato-conjunctivitis, etc.), and sepsis.

In order to illustrate the usefulness of the trifluoromethylketone derivatives (I) and their pharmaceutically acceptable salt, pharmacological test data thereof are shown below.

Test 1. : Protease Inhibition assay (in vitro)

(1) Method:

A buffer used throughout the assay was 0.1M HEPES (4-(2-hydroxyethyl)-1-piperazineethanesulfonic acid) containing 0.5M NaCl, pH 7.5. Twenty-five microliters of 2 mMmethoxysuccinyl-(Ala)$_2$-Pro-Val-p-nitroanilide (100 mM of dimethyl sulfoxide solution were diluted in the buffer) and 50 μl of sample (10 μl of sample in organic solvent was diluted 5-fold in the buffer) were mixed in wells of 96 well-microliter plate. An absorbance of the mixture in wavelength at 415 nmwas measured by a microplate reader (Corona Electric Co., Ibaraki, Japan). After the measurement 25 μl of 6 μg/ml human sputum elastase (HSE) was added and the mixture was allowed to stand for 30 minutes at room temperature. Then, the absorbance at 415 nm was measured. Percent inhibition by drug was determined by $100 \times (1-"r"$ inhibitor present/"r" inhibitor absent), where "r" is absorbance after 30 minutes incubation minus absorbance before enzyme addition. Effect of inhibitors against porcine pancree elastase (Type IV, 5 μg/ml final) was assayed similarly using N-succinyl-(Ala)$_3$-p-nitroanilide. HSE was obtained from elastin Products Company Inc., MO, U.S.A. All other substrate and protease were purchased from Sigma Chemicals Co.

| Inhibitory effect on several serine protease activity IC$_{50}$ (M) | | |
|---|---|---|
| Test Compound (Example No.) | Human sputum elastase | Porcine pancreas elastase |
| 1 | $4.5 \times 10^{-7}$ | $4.4 \times 10^{-6}$ |
| 3 | $9.8 \times 10^{-7}$ | $8.7 \times 10^{-6}$ |
| 4 | $1.4 \times 10^{-6}$ | $2.9 \times 10^{-6}$ |
| 5 | $3.0 \times 10^{-7}$ | $5.1 \times 10^{-6}$ |
| 6 | $4.3 \times 10^{-7}$ | $6.9 \times 10^{-6}$ |
| 7 | $3.2 \times 10^{-7}$ | $3.8 \times 10^{-6}$ |
| 8 | $8.7 \times 10^{-7}$ | $1.6 \times 10^{-5}$ |
| 9 | $8.7 \times 10^{-7}$ | $9.5 \times 10^{-6}$ |
| 10 | $8.0 \times 10^{-6}$ | $3.1 \times 10^{-4}$ |
| 13 | $7.2 \times 10^{-7}$ | $3.3 \times 10^{-6}$ |

-continued

| Inhibitory effect on several serine protease activity IC$_{50}$ (M) | | |
|---|---|---|
| Test Compound (Example No.) | Human sputum elastase | Porcine pancreas elastase |
| 15 | $6.1 \times 10^{-7}$ | $2.0 \times 10^{-6}$ |
| 16 | $7.1 \times 10^{-6}$ | $3.0 \times 10^{-5}$ |
| 17 | $1.1 \times 10^{-6}$ | $3.4 \times 10^{-6}$ |
| 18 | $6.1 \times 10^{-7}$ | $3.8 \times 10^{-6}$ |
| 19 | $6.8 \times 10^{-7}$ | $3.0 \times 10^{-6}$ |
| 20 | $8.9 \times 10^{-7}$ | $2.4 \times 10^{-6}$ |
| 21 | $1.2 \times 10^{-6}$ | $3.7 \times 10^{-6}$ |
| 22 | $6.8 \times 10^{-7}$ | $4.9 \times 10^{-6}$ |
| 23 | $8.1 \times 10^{-7}$ | $2.4 \times 10^{-6}$ |
| 24 | $1.4 \times 10^{-6}$ | $3.8 \times 10^{-6}$ |
| 27 | $2.4 \times 10^{-6}$ | $1.6 \times 10^{-5}$ |
| 29 | $2.4 \times 10^{-6}$ | $1.9 \times 10^{-5}$ |

Test 2. : Determination of the activity in elastase-induced pulmonary damage.

(1) Method:

Hamsters under pentobarbital anesthesia were used. Saline or saline-containing human sputum elastase was instilled intratracheally via a small incision in the ventral neck region using 1-ml syringe with a 27-gauge needle. After 3 hours, animals were sacrificed by $CO_2$ asphyxiation, each animal's trachea was reexposed. The lungs were then laveged using a 2.5-ml aliquot of saline and then withdrawing the saline, yielding a final volume of approximately 1.5 ml bronchoalveolar lavage (BAC) fluid from each animal.

The cells of BAL fluid were collected by centrifugation and were then diluted with distilled water to disrupt, and the hemoglobin contents determined spectrophotometrically at 541 nm.

Test drugs were dissolved in saline or methyl cellulose, and instilled intratracheally in the same manner as used to instill elastase, at 5 minutes before instillation of elastase.

(2) Result:

| Inhibitory effect on elastase-induced lung hemorrhage | | | | |
|---|---|---|---|---|
| Test Compound (Example No.) | 5 min. predose (μg/site) | Hemorrhage (OD541 nm) | % inhibition | ED$_{50}$ (μg/site) |
| Normal Control | | $0.6449 \pm 0.173$*** | — | |
| | | $14.66 \pm 1.68$ | — | |
| 13 | 1 | $11.63 \pm 1.99$ | 21.6 | 3.0 |
| | 10 | $4.217 \pm 1.02$** | 74.5 | |
| | 100 | $0.6384 \pm 0.222$*** | 100.0 | |
| Normal Control | | $0.8352 \pm 0.423$*** | — | |
| | | $12.89 \pm 1.44$ | — | |
| 19 | 1 | $11.59 \pm 1.40$ | 10.8 | |
| | 10 | $1.663 \pm 0.690$*** | 93.1 | 2.4 |
| | 100 | $0.2141 \pm 0.020$*** | 105.2 | |
| Normal Control | | $0.8352 \pm 0.423$*** | — | |
| | | $12.89 \pm 1.44$ | — | |
| 20 | 1 | $10.94 \pm 1.35$ | 16.1 | |
| | 10 | $2.522 \pm 0.803$*** | 86.0 | 2.5 |
| | 100 | $0.2680 \pm 0.050$*** | 104.7 | |
| Normal Control | | $0.6449 \pm 0.173$*** | — | |
| | | $14.66 \pm 1.68$ | — | |
| 21 | 1 | $12.76 \pm 1.11$ | 13.6 | |
| | 10 | $5.372 \pm 2.06$** | 66.3 | 4.5 |
| | 100 | $0.6476 \pm 0.129$*** | 100.0 | |
| Normal Control | | $0.9424 \pm 0.403$*** | — | |
| | | $11.05 \pm 1.40$ | — | |
| 23 | 1 | $9.435 \pm 0.941$ | 16.0 | |
| | 10 | $3.412 \pm 1.31$** | 75.6 | 3.2 |
| | 100 | $0.7258 \pm 0.303$*** | 102.1 | |
| Normal Control | | $0.3203 \pm 0.159$** | — | |
| | | $14.11 \pm 1.80$ | — | |
| 27 | 1 | $10.68 \pm 1.25$ | 24.8 | |

-continued

| Test Compound (Example No.) | 5 min. predose (μg/site) | Hemorrhage (OD541 nm) | % inhibition | $ED_{50}$ (μg/site) |
|---|---|---|---|---|
|  | 10 | 4.878 ± 0.917** | 66.9 | 3.7 |
|  | 100 | 0.3451 ± 0.084*** | 99.8 |  |
| Normal |  | 0.3199 ± 0.159*** | — |  |
| Control |  | 14.11 ± 1.80 | — |  |
| 29 | 1 | 12.05 ± 1.95 | 14.9 |  |
|  | 10 | 8.155 ± 1.76* | 43.2 | 17.9 |
|  | 100 | 4.545 ± 1.49** | 69.4 |  |

*$P < 0.05$, $P < 0.01$, *$P < 0.001$ (Student's t-test)

Test 3: Effect on human sputum elastase induced paw edema in mice.

(1) Materials and methods;

Male C57BL mice at the age of 7–8 weeks were obtained from Japan Clear Inc,.

Human sputum elastase (HSE) was purchased from Elastin Products Company, Inc,. The test drug was administered subcutaneously, and 15 minutes later, HSE was injected into the right hind footpad at the dosage of 20 Ng/site, and saline into the left hind footpad as the control. After 2 hours of HSE injection, the paw edema was measured with the dial thickness gage, and the difference of the thickness between right and left hind footpads was calculated.

(2) Results:

Effect on the elastase induced paw edema in mice

| Treatment of the compound of Example 19 (mg/kg) | n | Thickness of footpad ($\times 10^{-2}$ mm) | % Inhibition of paw edema |
|---|---|---|---|
| Control | 5 | 46.8 ± 5.76 |  |
| 1 | 5 | 43.8 ± 5.67 | 6.4 |
| 10 | 5 | 37.0 ± 13.41 | 20.9 |
| 100 | 5 | 27.0 ± 4.66* | 42.3 |

*$p < 0.05$ vs control group (Student's $t$ test)

Test 4: Effect on experimentally induced emphyseman in hamsters (1) Materials and methods:

Male golden Syrian hamsters, weighing approximately 120 g, were obtained from Japan SLC Inc,.

Porcine pancreatic elastase (PPE) was purchased from Elastin Products Company, Inc,. Dialferin was purchased from Japan ROche Inc,.

Hamsters were anesthetized intraperitoneally with Pentobarbital. The compound of Example 19 was dissolved in saline. Both prior art compounds A and B were suspended in 0.5 % methyl cellulose. The drugs were instilled intratracheally through the oral cavity, 5 minutes before 100 μg/site of PPE in 0.2 ml of saline instillation. Three weeks after PPE instillation, the hamsters were anesthetized with Pentobarbital. Respiratory mechanics were studied in supine hamsters using a whole body, constant-volume, variable pressure plethysmograph to measue volume. A water-filled esophageal catheter was used to estimate pleural pressure. Quasi-static deflation pressure-volume (P-V) curves were obtained by intraperitoneally administered Dialferin to suppress spontaneous breathing inflating the lungs to a transpulmonary pressure (PL) of 30 cm $H_2O$, permitting slow deflation to a PL of 0 cm $H_2O$ and gently aspirating to a PL of $-20$cm $H_2O$. Quasi-static lung compliance (Cst) was defined as the slope of the steep portion of the deflation P-V curve in the mid-volume range. Vital capacity was defined as the difference in lung volume between TLC25 (volume at PL=25cm $H_2O$) and RV-20 (volume at PL=$-20$cm $H_2O$).

(2) Results:

Pretreatment with the compound of Example 19 prevented the development of PPE-induced increases in lung mechanics in a dose dependent manner as shown in the following table. Considering Cst and VC values, the potency of the compound of Example 19 was superior to the prior art compounds A and B.

Effect on experimentally induced emphysema in hamsters

| Treatment (μg/site) | n | Cst (ml/cmH2O) | VC (ml) |
|---|---|---|---|
| Exp. 1 |  |  |  |
| Normal | 8 | 0.53 ± 0.02*** | 4.9 ± 0.1*** |
| Control | 8 | 1.54 ± 0.10 | 7.3 ± 0.2 |
| Compound of Example 19 |  |  |  |
| 1 | 8 | 1.39 ± 0.05(15%) | 7.0 ± 0.1(12%) |
| 10 | 8 | 0.70 ± 0.04(84%)*** | 5.8 ± 0.1(65%)*** |
| 100 | 7 | 0.53 ± 0.02(100%)*** | 5.0 ± 0.1(97%)*** |
| Exp. 2 |  |  |  |
| Normal | 8 | 0.51 ± 0.02*** | 4.6 ± 0.1*** |
| Control | 8 | 1.62 ± 0.12 | 6.8 ± 0.1 |
| Prior art Compound A |  |  |  |
| 100 | 8 | 1.55 ± 0.11(7%) | 6.9 ± 0.2(−1%) |
| 1000 | 8 | 1.22 ± 0.15(37%) | 6.6 ± 0.2(9%) |
| Exp. 3 |  |  |  |
| Normal | 8 | 0.49 ± 0.02** | 4.6 ± 0.2*** |
| Control | 6 | 1.18 ± 0.21 | 7.0 ± 0.2 |
| Prior art Compound B |  |  |  |
| 32 | 8 | 1.95 ± 0.08(32%) | 6.1 ± 0.3(39%)* |
| 320 | 8 | 0.74 ± 0.05(63%)* | 5.8 ± 0.2(49%)** |

Cst = Quasi static lung compliance, VC = Vital capacity
(%) = Inhibition
*$p < 0.05$, $p < 0.01$, *$p < 0.001$ vs Control (Student's $t$ test)

Prior art compound A (Japanese Kokai Tokkyo Koho No. 61-218518):

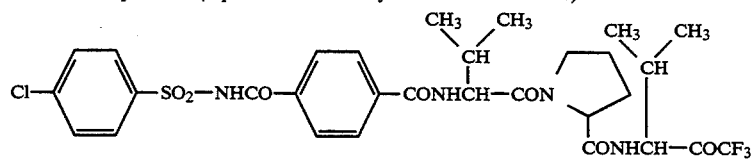

Prior art compound B (Japanese Kokai Tokkyo Koho No. 2-256657):

-continued

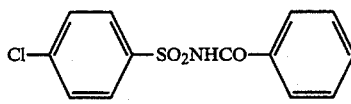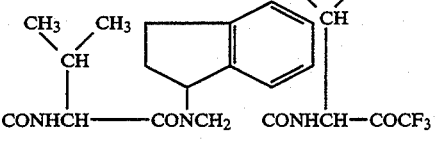

Pharmaceutical compositions of this invention can be used in a conventional pharmaceutical forms such as powders, fine granules, granules, tablets, dragee, injections, inhalations, microcapsules, capsules, suppository, solution, suspension, emulsion, syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweeting agents, lubricant (e.g. magnesium stearate, etc.) or the like, may be dispensed with said composition.

The dosage of said composition of this invention depends on the patient's age, body weight, condition, etc., and it is generally administered by the oral or inhale route at the daily dose level of 1 mg to 1 g as the object compound or its pharmaceutically acceptable salt, preferably 10 mg to 500 mg on the same basis, at the interval of 1 to 3 times a day. Typical unit doses may be 5 mg, 10 mg, 20 mg, 50 mg, 100 mg and the like, although these are only examples and not limitative.

The following Preparations and Examples are given for the purpose of illustrating this invention.

In the Preparations and Examples, the following abbreviations are used.
WSCD: 1-ethyl-3-(3-dimethylaminopropyl)carbodiimide
HOBT: N-hydroxybenzotriazole
DMF : N,N-dimethylformamide
DMSO: dimethylsulfoxide

Preparation 1

To a solution of N-(tert-butoxycarbonyl)-L-valine (10.86 g) and L-proline benzyl ester hydrochloride (12.09 g) in DMF (50 ml) were added HOBT (6.76 g) and WSCD (7.76 g) under ice-bath cooling. After being stirred at room temperature for 18 hours, the reaction mixture was concentrated under reduced pressure. The residue was dissolved in ethyl acetate (400 ml) and washed with 5% aqueous citric acid (200 ml) saturated aqueous sodium bicarbonate (200 ml). The solution was dried over magnesium sulfate and evaporated under reduced pressure to give N-(tert-butoxycarbonyl)-L-valyl-L-proline benzyl ester (20.06 g) as an oil.

TLC (Kiesel gel 60 F254 silica gel plate, Merck) The same meaning in the following Preparations and Examples, unless otherwise indicated) Rf: 0.62 (Hexane:AcOEt=2:1)

The following compounds were prepared by a similar method to that of Preparation 1.

Preparation 2

4-(Methoxycarbonyl)phenylcarbonyl-L-valyl-L-proline benzyl ester oil TLC Rf: 0.89 (CHCl$_3$:MeOH=10:1)

Preparation 3

3(RS)-[[4-(Methoxycarbonyl)phenylcarbonyl]-L-valyl-L-prolyl]amino -1,1,1-trifluoro-2(RS)-hydroxy-4-methylpentane
mp: 64°-67° C. TLC Rf : 0.63 and 0.60 (CHCl$_3$:MeOH=10:1)

Preparation 4

3(R or S)-[[4-(Methoxycarbonyl)phenylcarbonyl]-L-valyl-L-prolyl]amino-1,1,1-trifluoro-2(R or S)-hydroxy-4-methylpentane mp: 65°-75° C. TLC Rf 0.65 (CHCl$_3$:MeOH=10:1) $[a]_D^{22}$ :—56.23° (C=0.14, MeOH)

Preparation 5

3(R or S)- [[4-(Benzyloxycarbonylmethylaminocarbonyl)phenylcarbonyl]-L-valyl-L-prolyl]amino-1,1,1-trifluoro-2(R or S)-hydroxy-4 -methylpentane mp: 70°-80° C. TLC Rf : 0.65 (CHCl$_3$:MeOH=10:1) $[a]_D^{22}$: —46.59° (C=0.165, MeOH)

Preparation 6

3(R or S)-[[4-(Benzyloxycarbonylmethylaminocarbonyl)phenylcarbonyl ]-L-valyl-L-prolyl]amino-1,1,1-trifluoro-2(R or S)-hydroxy-4-methylpentane trifluoro-2(R or S)-hydroxy-4-methylpentane
mp: 80°-90° C. TLC Rf: 0.60 (CHCl$_3$:MeOH=10:1) $[a]_D^{22}$: —27.59° (C=0.165, MeOH)

Preparation 7

3(R or S)-[[4-(Methoxycarbonyl)phenylcarbonyl]-L-valyl-L-prolyl]amino-1,1,1-trifluoro-2(R or S)-hydroxy-4-methylpentane
mp: 68°-85° C. TLC Rf: 0.60 [CHCl$_3$:MeOH=10:1) $[a]_D^{22}$: —42.63° (C=0.175, MeOH)

Preparation 8

N-(tert-Butoxycarbonyl)-L-valyl-L-proline benzyl ester (20.0 g) was dissolved in 4N hydrogen chloride in dioxane (30 ml) under ice bath cooling. After being stirred at room temperature for one hour, the reaction mixture was evaporated under reduced pressure. The residue was pulverized with ether to give L-valyl-L-proline benzyl ester hydrochloride (14.56 g).
mp: 66°-69° C. TLC Rf : 0.55 (CHCl$_3$: MeOH=10:1)

Preparation 9

A solution of N-4-(methoxycarbonyl)phenylcarbonyl-L-valyl-L-proline benzyl ester (18.53 g) in methanol (150 ml) was hydrogenated over 10% palladium on carbon (1.0 g) at 3 atmosphere pressure of hydrogen for 1.5 hours at room temperature. After the catalyst was removed by filtration, the filtrate was evaporated under reduced pressure to give 4-(methoxycarbonyl)phenylcarbonyl-L-valyl-L-proline (14.20 g).
mp: 68°-71° C. TLC Rf : 0.27 (CHCl$_3$:MeOH=10:1)

Preparation 10

To a solution of oxalyl chloride (0.82 ml) in dichloromethane (5 ml) were added dimethylsulfoxide (1.34 ml) and a solution of 3(RS)-[[4-(4-methoxycarbonyl)phenylcarbonyl]-L-valyl-L-prolyl]amino-1,1,1-trifluoro2(RS)-hydroxy-4-methylpentane methylpentane (2.5 g) in dichloromethane (10 ml) at −70° C. successively. After the mixture was stirred for one hour at −40° C., triethylamine (2.63 ml) was added. The mixture was stirred for an additional 30 minutes at the same temperature and washed with 0.5N hydrochloric acid (15 ml) and 5% sodium bicarbonate aqueous solution (15 ml). The organic layer was dried over magnesium sulfate and evaporated under reduced pressure. The residue was purified with silica gel (50 g) column chromatography (chloroform:methanol=50:1) to give 3(RS)-[[4-(4-methoxycarbonyl)phenylcarbonyl]-L-valyl-L-prolyl]amino-1,1,1-trifluoro-4-methyl-2-oxopentane (2.18 g).

mp:67°-70° C. TLC Rf : 0.51 (CHCl$_3$:MeOH=10:1)

Preparation 11

To a solution of 3(RS)-[[4-(4-methoxycarbonyl)-phenylcarbonyl]-L-valyl-L-prolyl]amino-1,1,1-trifluoro-4methyl-2-oxopentane (2.1 g) in methanol (40 ml) was added 1N aqueous sodium hydroxide (15 ml) under ice-bath cooling. After the mixture was stirred at room temperature for 2 hours, methanol was evaporated. The concentrate was washed with ether (30 ml), then acidified to pH 2 with 1N hydrochloric acid. The aqueous solution was extracted with ethyl acetate (20 ml). The extract was washed with brine (10 ml), dried over magnesium sulfate and concentrated under reduced pressure to give 3(RS)-[(4-carboxyphenylcarbonyl)-L-valyl-L-prolyl]amino -1,1,1-trifluoro-4-methyl-2-oxopentane (1.94 g).

mp: 215°-220° C. TLC Rf : 0.63 (CHCl$_3$:MeOH:AcOH=8:2:1)

The following compounds were prepared by a similar method to that of Preparation 11.

Preparation 12

3(R or S)-[[4-(Carboxy)phenylcarbonyl]-L-valyl-L-prolyl]amino-1,1,1-trifluoro-2(R or S)-hydroxy-4-methylpentane (0.61 g)

mp: 266°-269°C. TLC Rf: 0.42 (Benzene:EtOAc:AcOH=20:20:1) [a]$_D^{22}$: −49.71° (C=0.1, MeOH)

Preparation 13

3(R or S)-[[4-(Carboxy)phenylcarbonyl ]-L-valyl-L-prolyl]amino-1,1,1-trifluoro-2(R or S)-hydroxy-4-methylpentane mp: 265°-268°C. TLC Rf: 0.40 ( Benzene: EtOAc:AcOH=20:20:1) [a]$_D^{22}$: −64.25° (C=0.16, MeOH)

Preparation 14

A solution of 28% sodium methoxide in methanol (3.0 ml) was added to a solution of 3(RS)-amino-1,1,1-trifluoro-2(RS)-hydroxy-4-methylpentane hydrochloride (3.2 g) in ethanol (30 ml) at room temperature. After removal of the precipitated sodium chloride by filtration, (2R,3R)-L-tartaric acid (2.3 g) was added to the filtrate. The mixture was warmed until tartaric acid was dissolved and filtrated. The liltrate was allowed to stand for 5 hours at room temperature. The precipitated crystalline solid (1.94 g) was collected by filtration and dissolved in 1N aqueous sodium hydroxide. The solution was extracted with ethyl acetate (10 ml) and the extract was mixed with 4N-hydrogen chloride in ethyl acetate. After removal of ethyl acetate, the residue was pulverized with diisopropyl ether (10 ml) to give 3(R or S)-amino-1,1,1-trifluoro-2(R or S)-4-methylpentane hydrochloride (1.03 g).

mp: 165°-170° C. TLC Rf : 0.50 (CHCl$_3$:MeOH=10:1) [a]$_D^{22}$: +11.39° (C=0.13, MeOH)

The following compound was prepared by a similar method to that of Preparation 14.

Preparation 15

3(R or S)-Amino-1,1,1-trifluoro-2(R or S)-4-methylpentane hydrochloride mp: 165°-170° C. TLC Rf : 0.55 (CHCl$_3$:MeOH=10:1) [a]$_D^{22}$: −10.56° (C=1.05, MeOH)

Preparation 16

To a solution of methyl p-aminobenzoate (0.4 g) in tetrahydrofuran (10 ml) was added trichloromethylchloroformate (0.31 g) and the mixture was allowed to stand overnight at room temperature. L-Valine benzyl ester (0.54 g) was added to the solution and the pH of the mixture was neutralized with triethylamine. After being stirred for 30 minutes at room temperature, the mixture was concentrated under reduced pressure and the residue was extracted with ethyl acetate (10 ml). The extract was washed with 1N-hydrochloric acid (10 ml) and aqueous sodium bicarbonate (10 ml) and concentrated to dryness to give 4-(methoxycarbonyl)-phenylaminocarbonyl-L-valine benzyl ester (1.17 g).

TLC Rf: 0.55 (CHCl$_3$:MeOH=10:1, V/V)

Preparation 17

4-(Methoxycarbonyl)phenylaminocarbonyl-L-valine (0.83 g) was prepared from 4-(methoxycarbonyl)-phenylaminocarbonyl) -L-valine benzyl ester (1 g) by a similar method to that of Preparation 9.

TLC Rf: 0.3 (CHCl$_3$:MeOH:H$_2$O =65:25:4) Oil

Preparation 18

[4-(Methoxycarbonyl)phenylaminocarbonyl]-L-valyl -L-proline benzyl ester (1.0 g) was prepared from 4-(methoxycarbonyl)phenylaminocarbonyl-L-valine (0.83 g) and L-proline benzyl ester hydrochloride (0.65 g) by a similar method to that of Preparation 1.

TLC Rf : 0.60 (CHCl$_3$:MeOH=10:1) Oil

Preparation 19

[4-(Methoxycarbonyl)phenylaminocarbonyl ]-L-valyl-L-proline (0.69 g) was prepared from [4-(methoxycarbonyl)phenylaminocarbonyl]-L-valyl-L-proline benzyl ester (1.0 g) by a similar method to that of Preparation 9.

TLC Rf : 0.35 (CHCl$_3$:MeOH:H$_2$O=65:25:4) Oil

Preparation 20

3(RS)-[[4-(Methoxycarbonyl)phenylaminocarbonyl ]-L-valyl-L-propyl]amino-1,1,1-trifluoro-2(RS)-hydroxy-4-methylpentane (1.03 g) was prepared from [4-(methoxycarbonyl]phenylaminocarbonyl]-L-valyl-L-proline (0.69 g) and 3(RS)-amino-1,1,1-trifluoro-2(RS)-hydroxy-4-methylpentane hydrochloride (0.37 g) by a similar method to that of Preparation 1.

TLC Rf : 0.45 (CHCl$_3$:MeOH=10:1) Oil

Preparation 21

3(RS)-[[4-(Methoxycarbonyl)phenylaminocarbonyl]-L-valyl -L-prolyl]amino-1,1,1-trifluoro-2-oxo-4-methylpentane (0.98 g) was prepared from 3(RS)-[[4-(methoxycarbonyl)phenylaminocarbonyl)-L-valyl -L-prolyl]amino-1,1,1-trifluoro-2(RS)-hydroxy-4-methylpentane (1.0 g) by a similar method to that of Preparation 10.

mp: 90°–100° C. TLC Rf: 0.50 (CHCl$_3$:MeOH=10:1)

Preparation 22

3(RS)-[[4-(Carboxy)phenylaminocarbonyl]-L-valyl-L-prolyl]amino-1,1,1-trifluoro-2-oxo-4-methylpentane (0.2 g) was prepared from 3(RS)-[[4-(methoxycarbonyl)phenylaminocarbonyl]-L-valyl -L-valyl-L-prolyl]amino]-1,1,1-trifluoro-2-oxo-4-methylpentane (0.3 g) by a similar method to that of Preparation 11.

mp : 125°–130° C. TLC Rf : 0.50 (CHCl$_3$: MeOH:-H$_2$O=65:25:4)

Preparation 23

To a solution of N-(tert-butoxycarbonyl)-L-valine (4.35 g) and triethylamine (2.13 g) in dry CH$_2$Cl$_2$ (40 ml) was added isobutyl chloroformate (2.87 g) at −20° C. After being stirred at same temperature for 30 minutes, a solution of N-(2-indanyl)glycine benzyl ester (5.37 g) in dry CH$_2$Cl$_2$ (20 ml) was added at −20° C. The reaction mixture was stirred at −10° C. for one hour then at room temperature for 4 hours. After the reaction mixture was evaporated under reduced pressure, the residue was dissolved in ethyl acetate (100 ml) and washed with saturated aqueous sodium bicarbonate (100 ml×2). The organic layer was dried over magnesium sulfate and evaporated under reduced pressure. The residue was purified with silica gel (50 g) column chromatography (CHCl$_3$:AcOEt=10:1) to give N-(tert-butoxycarbonyl)-L-valyl-N-(2-indanyl)glycine benzyl ester (2.20 g) as an oil.

TLC Rf: 0.78 (Hexane:AcOEt=2:1)

Preparation 24

L-Valyl-N-(2-indanyl)glycine benzyl ester hydrochloride (1.83 g) was prepared from N-(tert-butoxycarbonyl)-L-valyl-N-(2-indanyl)glycine benzyl ester (2.14 g) by a similar method to that of Preparation 8.

mp: 162°–163° C. TLC Rf : 0.58 (CHCl$_3$:MeOH=10:1)

Preparation 25

N-[4-(Methoxycarbonyl)phenylcarbonyl]-L-valyl-N-(2-indanyl)glycine benzyl ester (1.24 g) was prepared from L-valyl-N-(2-indanyl)glycine benzyl ester hydrochloride (1.80 g) and terephthalic acid mono methyl ester (0.86 g) by a similar method to that of Preparation 1.

mp: 72°–76° C. TLC Rf: 0.29 (CHCl$_3$)

Preparation 26

N-[4-(Methoxycarbonyl)phenylcarbonyl]-L-valyl-N-(2-indanyl)glycine (0.83 g) was prepared from N-[4-(methoxycarbonyl)phenylcarbonyl]-L-valyl-N-(2-indanyl)glycine benzyl ester (1.20 g) by a similar method to that of Preparation 9.

mp: 163°–164° C. TLC Rf : 0.48 (CHCl$_3$:MeOH=10:1)

Preparation 27

3(RS)-[[4-(Methoxycarbonyl)phenylcarbonyl]-L-valyl-N-(2-indanyl)glycyl]amino-1,1,1-trifluoro-2(RS)-hydroxy-4-methylpentane (1.06 g) was prepared from N-[4-(methoxycarbonyl)phenylcarbonyl]-L-valyl-N-(2-indanyl) glycine (0.80 g) and 3(RS)-amino-1,1,1-trifluoro-2(RS) -hydroxy-4-methylpentane hydrochloride (385 mg) by a similar method to that of Preparation 1.

mp: 76°–78° C. TLC Rf: 0.71 (CHCl$_3$: MeOH=10:1)

Preparation 28

3(RS)-[[4-(Methoxycarbonyl)phenylcarbonyl]-L-valyl-N(2-indanyl)glycyl]amino-1,1,1-trifluoro-4-methyl-2-oxopentane (0.84 g) was prepared from 3(RS)-[[4-(methoxycarbonyl)phenylcarbonyl]-L-valyl-N -(2-indanyl)glycyl]-amino-1,1,1-trifluoro-2(RS) -hydroxy-4-methylpentane (1.03 g) by a similar method to that of Preparation 10.

mp: 62°–64° C. TLC Rf : 0.74 (CHCl$_3$: MeOH=10:1)

Preparation 29

3(RS)-[(4-Carboxyphenylcarbonyl)-L-valyl-N-(2-indanyl) glycyl]amino-1,1,1-trifluoro-4-methyl-2-oxopentane (0.76 g) was prepared from 3(RS)-[[4-(methoxycarbonyl)phenylcarbonyl)-L-valyl-N-(2-indanyl)-glycyl]amino-1,1,1-trifluoro-4-methyl-2-oxypentane (0.83 g) by a similar method to that of Preparation 11.

mp: 84°–86° C. TLC Rf : 0.15 (CHCl$_3$:MeOH=10:1)

Example 1

To a mixture of glycine benzyl ester p-toluenesulfonate (66 mg) and 3(RS)-[(4-carboxyphenylcarbonyl)-L-valyl-L-prolyl]amino-1,1,1-trifluoro-4-methyl-2-oxopentane (100 mg) in DMF (6 ml) were added HOBT (26 mg) and WSCD (30 mg) under ice-bath cooling. After being stirred at room temperature for 4 hours, the mixture was concentrated under reduced pressure. The residue was dissolved in ethyl acetate (30 ml) and washed with 5% aqueous citric acid (20 ml), water (20 ml), 5% aqueous sodium bicarbonate (20 ml) and brine (20 ml). The solution was dried over magnesium sulfate and evaporated under reduced pressure to give 3(RS)-[[4-[(benzyloxycarbonyl)methylaminocarbonyl]phenylcarbonyl]-L-valyl-L-prolyl]amino-1,1,1-trifluoro-4-methyl-2-oxopentane (125 mg).

mp: 77°–78° C. TLC Rf: 0.56 (CHCl$_3$:MeOH=10:1)

The following compounds were prepared by a similar method to that of Example 1.

Example 2

3 ( RS ) - [[4-[[2-(4-Morpholino)ethyl]aminocarbonyl]phenylcarbonyl]- phenylcarbonyl]L-valyl-L-prolyl]amino-1,1,1-trifluoro-4-methyl-2-oxopentane mp : 98°–102° C. TLC Rf: 0.24 (CHCl$_3$:MeOH=10:1)

Example 3

3(RS)-[[4-[(3-Benzoylmethoxycarbonyl)-propylaminocarbonyl ]phenylcarbonyl]-L-valyl-L-prolyl]amino-1,1,1-trifluoro-4-4-methyl-2-oxopentane mp: 70°–73° C. TLC Rf: 0.71 (CHCl$_3$: MeOH=10:1)

Example 4

3(RS)-[[4-[(4-Morpholino)aminocarbonyl]phenylcarbonyl]-L-valyl-L-prolyl]amino-1,1,1trifluoro-4-methyl-2-oxopentane mp: 191°–193° C. TLC RE : 0.59 (CHCl$_3$:MeOH=10:1)

Example 5

3(RS)-[[4-[(4-Chlorobenzyl)aminocarbonyl]phenylcarbonyl]-L-valyl-L-prolyl]amino-1,1,1-trifluoro-4-methyl-2-oxopentane mp: 87°-89° C. TLC Rf : 0.43 (CHCl$_3$:MeOH=10:1)

Example 6

3(RS)-[[4-[(4-Nitrobenzyl)aminocarbonyl]phenylcarbonyl]-L-valyl-L-prolyl]amino-1,1,1-trifluoro-4-methyl-2-oxopentane mp: 94°-96° C. TLC Rf : 0.57 (CHCl$_3$:MeOH=10:1)

Example 7

3 (RS) -[[4-[(4-Chlorophenyl)aminocarbonyl]phenylcarbonyl]-phenylcarbonyl]-L-valyl-L-prolyl]amino-1,1,1-trifluoro-4-methyl-2-oxopentane mp : 71°-72 C. TLC Rf : 0.79 (CHCl$_3$: MeOH=10:1)

Example 8

3(RS)-[[4-[[(1(R)-Benzyloxycarbonyl)-2-phenyl]ethylaminocarbonyl]]phenylcarbonyl]-L-valyl-L-prolyl]amino -1,1,1-trifluro-4-methyl-2-oxopentane mp: 65°-67° C. TLC Rf : 0.82 (CHCl$_3$:MeOH=10:1)

Example 9

3(RS)-[[4-[[(1(S)-Benzyloxycarbonyl)-2-phenyl]ethylaminocarbonyl]-L-valyl -L-prolyl]amino -1,1,1-trifluoro-4-methyl-2-oxopentane mp: 108°-110° C. TLC Rf : 0.82 (CHCl$_3$:MeOH=10:1)

Example 10

3(RS)-[[4-[[1(S),B-bis(Benzyloxycarbonyl)propyl]aminocarbonyl]phenylcarbonyl]-L-valyl-L-prolyl]amino -1,1,1-trifluoro-4-methyl-2-oxopentane mp: 58°-60° C. TLC Rf : 0.83 (CHCl$_3$:MeOH=10:1)

Example 11

To a solution of oxalyl chloride ( 0.09 ml) in dichloromethane (2 ml) were added dimethylsulfoxide (0.15 ml) and a solution of 3(R or S)-[[4-(benzyloxycarbonylmethylaminocarbonyl) phenylcarbonyl]-L-valyl-L-prolyl]amino 1,1,1-trifluoro-2(R or S)-hydroxy -4-methylpentane (0.35 g) in dichloromethane (4 ml) at 70° C. successively. After the mixture was stirred for one hour at −40° C., triethylamine (0.29 ml) was added. The mixture was stirred for an additional 30 minutes at the same temperature and washed with 0.5N hydrochloric acid (15 ml) and 5% sodium bicarbonate aqueous solution (15 ml). The organic layer was dried over magnesium sulfate and evaporated under reduced pressure. The residue was purified with silica gel (20 g) column chromatography (Chloroform:methanol=50:1) to give 3(R or S)-[[4-(benzyloxycarbonylmethylaminocarbonyl) phenylcarbonyl]-L-valyl-L-proyl]amino-1,1,1-trifluoro-2-oxo-4-methylpentane (0.22 g).

mp: 159°-161° C. TLC Rf: 0.63 (CHCl$_3$: MeOH=10:1) [a]$_D^{22}$: −39.66° (C=0.105, MeOH)

The following compound was prepared by a similar method to that of Example 11.

Example 12

3(R or S)-[[4-(Benzyloxycarbonylmethylaminocarbonyl)phenylcarbonyl) -L-valyl-L-prolyl]amino-1,1,1-trifluoro-2-oxo-4-methylpentane mp: 141°-143° C. TLC Rf : 0.68 (CHCl$_3$: MeOH=10:1) [a]$_D^{22}$: −41.90° (C=0.15, MeOH)

Example 13

A solution of 3(RS)-[[4-[(benzyloxycarbonyl)methylaminocarbonyl]phenylcarbonyl]-L-valyl-L-prolyl]-amino-1,1,1-trifluoro-4-methyl-2-oxopentane (70 mg) in a mixture of methanol (10 ml) and water (1 ml) was hydrogenated over 10% palladium on carbon (1.0 g) at 3 atmosphere pressure of hydrogen for 3 hours at room temperature. After the catalyst was removed by filtration, the filtrate was evaporated under reduced pressure to give 3(RS)-[[4-(carboxymethylaminocarbonyl)phenylcarbonyl]-L-valyl-L-prolyl]amino-1,1,1-trifluoro-4-methyl-2-oxopentane (61 mg).

mp: 99°-103° C. TLC Rf: 0.17 (CHCl$_3$: MeOH:AcOH=8:1:1)

Example 14

To a solution of 3(RS)-[[4-[(3-benzoylmethoxycarbonyl)propylaminocarbonyl]phenylcarbonyl]-L-valyl-L-prolyl]amino-1,1,1-trifluoro-4-methyl-2-oxopentane (120 mg) in acetic acid (5 ml) was added zinc powder (120 mg) under ice-bath cooling. After the mixture was stirred at room temperature for 2 hours, zinc was removed by filtration. The liltrate was evaporated under reduced pressure to give 3(RS)-[[4-[(3-carboxypropyl)-aminocarbonyl ]phenylcarbonyl]-L-valyl-L-prolyl]amino -1,1,1-trifluoro-4-methyl-2-oxopentane (95 mg).

mp: 84°-86° C. TLC Rf : 0.32 (CHCl$_3$: MeOH:AcOH=8:1:1)

The following compounds were prepared by a similar method to that of Example 13.

Example 15

3(R or S)-[[4-(Carboxymethylaminocarbonyl)-phenylcarbonyl -L-valyl-L-prolyl-]amino-1,1,1-trifluoro-2-oxo-4-methylpentane mp: 75°-120° C. TLC (RP-18 WF$_{254}$S (made by E. Merck) Rf: 0.55 (MeOH:H$_2$O=6:5) [a]$_D^{22}$: −35.10° (C=0.105, MeOH)

Example 16

3(R or S)-[[4-(Carboxymethylaminocarbonyl)phenylcarbonyl]-L-valyl-L-prolyl]amino-1,1,1-trifluoro-2-oxo-4-methylpentane mp: 90°-110° C. TLC (RP-18 WF$_{254}$S (made by E. Merck) Rf : 0.50 (MeOH:H$_2$O=6:5) [a]$_D^{22}$: −50.04° (C=0.115, MeOH)

Example 17

3(RS)-[[4-[(1(S),3-Dicarboxypropyl)aminocarbonyl]-phenylcarbonyl]-L-valyl-L-prolyl]amino-1,1,1-trifluoro -4-methyl-2-oxopentane mp: 74°-76° C. TLC Rf : 0.13 (CHCl$_3$: MeOH:AcOH=8:1:1)

Example 18

A solution of 3(RS)-[[4-[(4-nitrobenzyl)aminocarbonyl]phenylcarbonyl]-L-valyl-L-prolyl]amino -1,1,1-trifluoro-4-methyl-2-oxopentane (50 mg) in methanol (10 ml) was hydrogenated over 10% palladium on carbon (10 mg) at 4 atmosphere pressure of hydrogen for 2 hours. The catalyst was removed by filtration and the liltrate was evaporated under reduced pressure to give 3(RS)-[[4-[(4aminobenzyl)aminocarbonyl]phenylcarbonyl]-L-valyl-L-prolyl]amino-1,1,1-trifluoro-4-methyl-2-oxopentane (46 mg).

mp: 90°-92° C. TLC Rf : 0.44 (CHCl$_3$: MeOH:AcOH=8:1:1)

Example 19

To a solution of 3(RS)-[[4-(carboxymethylaminocarbonyl)phenylcarbonyl]-L-valyl-L-prolyl]amino-1,1,1trifluoro-4-methyl-2-oxopentane (0.50 g) in water (10 ml) was added 1N aqueous sodium hydroxide (0.88 ml) at room temperature. The solution was lyophilized to give sodium salt of starting material (0.52 g).

mp: >230° C. TLC Rf : 0.17 (CHCl$_3$:MeOH:AcOH=8:1:1)

The following compound was prepared by a similar method to that of Example 19.

Example 20

A sodium salt of 3(RS)-[[4-[(3-carboxypropyl)aminocarbonyl]phenylcarbonyl]-L-valyl-L-prolyl]amino 1,1,1-trifluoro-4-methyl-2-oxopentane mp: 66°-69° C. TLC Rf : 0.32 (CHCl$_3$: MeOH:AcOH=8:1:1)

Example 21

To a solution of 3(RS)-[[4-[[2-(4-morpholino)ethyl]aminocarbonyl]phenylcarbonyl]-L-valyl-L-prolyl]amino 1,1,1-trifluoro-4-methyl-2-oxopentane (80 mg) in 1,4-dioxane (1 ml) was added 4N-hydrogen chloride in dioxane (0.1 ml). The mixture was stirred at room temperature for 10 minutes, and evaporated to give 3(RS)-[[4-[[2-(4-morpholino)ethyl]aminocarbonyl]-phenylcarbonyl]-L-valyl-L-prolyl]amino-1,1,1-trifluoro-4-methyl-2-oxopentane hydrochloride (83 mg).

mp: 64°-65° C. TLC Rf : 0.24 (CHCl$_3$: MeOH=10:1)

Example 22

3(RS)-[[4-(Benzyloxycarbonylmethylaminocarbonyl)phenylaminocarbonyl ]-L-valyl-L-prolyl]amino-1,1,1-trifluoro -2-oxo-4-methylpentane (0.25 g) was prepared from 3(RS)-[[4-(carboxy)phenylaminocarbonyl]-L-valyl-L-prolyl]-amino-1,1,1-trifluoro-2-oxo-4-methylpentane (0.2 g) and glycine benzyl ester para-toluenesulfonate (0.13 g) by a similar method to that of Example 1.

mp: 65°-70° C. TLC Rf : 0.15 (CHCl$_3$:MeOH=10:1)

Example 23

3(RS)-[[4-(Carboxymethylaminocarbonyl)-phenylaminocarbonyl] -L-valyl-L-prolyl]amino-1,1,1-trifluoro-2-oxo-4-methylpentane (0.14 g) was prepared from 3(RS)-[[4-(benzyloxycarbonylmethylaminocarbonyl)phenylaminocarbonyl)]-L-valyl-L-prolyl]amino-1,1,1 -trifluoro-2-oxo-4-methylpentane (0.2 g) by a similar method to that of Example 13.

mp: 98°-128° C. TLC Rf : 0.25 (CHCl$_3$: MeOH:H$_2$O=65:25:4)

Example 24

3(RS)-[[4-(Dimethylaminocarbonylmethylaminocarbonyl)phenylaminocarbonyl) -L-valyl-L-prolyl]amino-1,1,1 -trifluoro-2-oxo-4-methylpentane (0.03 g) was prepared from 3(RS)-[[4-(carboxymethylaminocarbonyl)-phenylaminocarbonyl ]-L-valyl-L-prolyl]amino-1,1,1 -trifluoro-2-oxo-4methylpentane (0.08 g) and dimethylamine hydrochloride (0.012 g) by a similar method to that of Example 1.

mp: 115°-125° C. TLC Rf : 0.20 (CHCl$_3$: MeOH=10:1)

Example 25

3(RS)-[[4-[(Benzyloxycarbonyl)methylaminocarbonyl]phenylcarbonyl]-L-valyl-N-(2-indanyl)glycyl]amino-1,1,1 -trifluoro-4-methyl-2-oxopentane (250 mg) was prepared from glycine benzyl ester p-toluenesulfonate (118 mg) and 3(RS)-[(4-carboxyphenylcarbonyl)-L-valyl-N-(2-indanyl)glycyl]amino-1,1,1-trifluoro-4-methyl-2-oxopentane (206 mg) by a similar method to that of Example 1.

mp: 64°-66° C. TLC Rf : 0.81 (CHCl$_3$: MeOH=10:1) White powder

Example 26

3 (RS) - [[4-(Carboxymethylaminocarbonyl)phenylcarbonyl ]-L-valyl-N- (2-indanylglycyl]amino- 1,1,1 -trifluoro-4-methyl-2-oxopentane (195 mg) was prepared from 3(RS)-[[4-[(benzyloxycarbonyl)methylaminocarbonyl]-phenylcarbonyl ]-L-valyl-N-(2-indanyl)glycyl]amino-1,1,1-trifluoro-4-methyl-2-oxopentane (220 mg) by a similar method to that of Example 13.

mp: 88°-91 C. TLC Rf : 0.25 (CHCl$_3$: MeOH:AcOH=16:1:1)

Example 27

A sodium salt of 3(RS)-[[4-(carboxymethylaminocarbonyl) phenylcarbonyl]-L-valyl-N-(2-indanyl)glycyl]-amino-1,1,1-trifluoro-4-methyl-2-oxopentane (160 mg) was prepared by a similar method to that of Example 19.

mp: 203°-205° C. TLC Rf : 0.25 (CHCl$_3$: MeOH:AcOH=16:1:1)

Example 28

3(RS)-[[4-[[2-(4-Morpholino)ethyl]aminocarbonyl]-phenylcarbonyl]-L-valyl-N-(2-indanyl)glycyl]amino-1,1,1 -trifluoro-4-methyl-2-oxopentane (180 mg) was prepared from 4-(2-aminoethyl)morpholine (46 mg) and 3(RS)-[(4-carboxyphenylcarbonyl)-L-valyl-N-(2-indanyl)-glycyl ]amino-1,1,1-trifluoro-4-methyl-2-oxopentane (206 mg) by a similar method to that of Example 1.

mp: 76°-80° C. TLC Rf: 0.38 (CHCl$_3$: MeOH=10:1)

Example 29

A hydrochloride of 3(RS)-[[4-[[2-(4-morpholino)ethyl ]aminocarbonyl]phenylcarbonyl]-L-valyl-N-(2-indanyl)glycyl]amino-1,1,1-trifluoro-4-methyl-2-oxopentane (170 mg) was prepared by a similar method to that of Example 21.

mp: 96°-99° C. TLC Rf : 0.38 (CHCl$_3$: MeOH=10:1)

Example 30

3(RS)-[[4-(ethoxycarbonyl)methylaminocarbonyl]-phenylcarbonyl]-L-valyl-L-prolyl]amino-1,1,1 -trifluoro-4-methyl-2-oxopentane was prepared by a similar method to that of Example 1.

mp: 96°-99° C.

Example 31

To a solution of 3(RS)-[[4-(ethoxycarbonyl)methylamminocarbonyl]phenylcarbonyl]-L-valyl-L-prolyl]amino-1,1,1-trifluoro-4-methyl-2-oxopentane (5.0 g) in methylene chloride (60 ml), methanol (10 ml) and water (25 ml) was added aqueous sodium hydroxide (NaOH 0.6 g in water (5 ml)) under ice-bath cooling. After the reaction mixture was stirred at 0°-10° C. for 10 minutes, it was adjusted to pH 9 with 6N hydrochloric acid and then aqueous solution was washed with methylene chloride (60 ml). To the aqueous solution were added sodium chloride (5 g) and ethylacetate (60 ml), and then the mixture was acidified to pH 2 with 6N hydrochloric acid. Ethyl acetate solution was washed with brine (30 ml), dried over magnesium sulfate and concentrated under reduced pressure to the volume of 20 ml. The concentrated solution was added dropwise to isopropyl ether (225 ml) at room temperature. Precipitate was filtered and then dried to give 3(RS)-[[4-(carboxymethylaminocarbonylphenylcarbonyl]-L-valyl-L-prolyl-]amino-1,1,1-trifluoro-4-methyl -2-oxopentane (3.24 g).

mp: 99°–103° C.

We claim:

1. A pharmaceutical composition comprising as an effective ingredient a trifluoromethylketone compound of the formula:

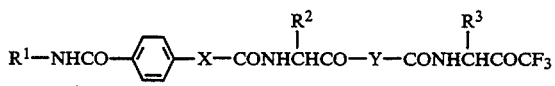

wherein $R^1$ is $C_{1-6}$ alkyl which has one or two substituents selected from carboxy, esterified carboxy and di-$C_{1-6}$ alkylcarbamoyl; phenyl($C_{1-6}$) alkyl, the phenyl moiety of which may have halogen or nitro or amino substituents and the alkyl moiety of which may have carboxy or esterified carboxy substituents; halo-phenyl; morpholino; or morpholino($C_{1-6}$) alkyl, $R^2$ and $R^3$ are each $C_{1-6}$ alkyl, X is — or —NH—, and

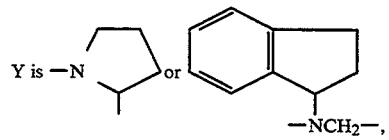

and pharmaceutically acceptable salts thereof; and a pharmaceutically acceptable carrier or excipient.

2. A pharmaceutical composition according to claim 1, wherein said trifluoromethylketone compound has the formula:
wherein $R^1$ is $C_{1-6}$ alkyl which has one or two substituents selected from carboxy, esterified carboxy and di-$C_{1-6}$ alkylcarbamoyl; phenyl($C_{1-6}$) alkyl, the phenyl moiety of which may have halogen or nitro or amino substituents and the alkyl moiety of which may have carboxy or esterified carboxy substituents; halophenyl; morpholino; or morpholino($C_{1-6}$)alkyl, and $R^2$ and $R^3$ are each $C_{1-6}$ alkyl, and pharmaceutically acceptable salts thereof.

3. A pharmaceutical composition according to claim 2, wherein in said trifluoromethylketone compound $R^1$ is $C_{1-6}$ alkyl which has carboxy or esterified carboxy substituents, and $R^2$ and $R^3$ are each $C_{1-6}$ alkyl.

4. A pharmaceutical composition according to claim 3, wherein in said trifluoromethylketone compound $R^1$ is carboxymethyl, and $R^2$ and $R^3$ ar each isopropyl.

5. A pharmaceutical composition according to claim 4, wherein said trifluoromethylketone compound is 3(RS)-[[4(carboxymethylaminocarbonyl)phenylcarbonyl]-L-valyl-L-prolyl]amino-1,1,1-trifluoro-4-methyl-2-oxopentane.

6. A pharmaceutical composition according to claim 4, wherein said trifluoromethylketone compound is a sodium salt of 3(RS)-[[4-carboxymethylaminocarbonyl)phenylcarbonyl]-L-valyl-L-prolyl]amino-1,1,1-trifluoro-4-methyl-2-oxopentane.

* * * * *